United States Patent [19]

Himpens et al.

[11] Patent Number: 5,397,331
[45] Date of Patent: Mar. 14, 1995

[54] SUPPORTING DEVICE AND APPARATUS FOR INSERTING THE DEVICE

[75] Inventors: Jacques Himpens, Lovendegem, Belgium; Jorgen Dilling-Hansen, Roskilde, Denmark

[73] Assignee: Cook Incorporated, Bloomington, Ind.

[21] Appl. No.: 981,192

[22] Filed: Nov. 25, 1992

[30] Foreign Application Priority Data

Nov. 25, 1991 [DK] Denmark ............... 1914/91

[51] Int. Cl.⁶ .............................................. A61B 17/00
[52] U.S. Cl. ................................... 606/151; 606/213; 606/232; 128/899; 623/11
[58] Field of Search ................... 606/1, 151, 157, 213, 606/215, 216, 200, 232; 128/899, 887; 623/1, 11

[56] References Cited

U.S. PATENT DOCUMENTS

| | | | |
|---|---|---|---|
| 4,577,631 | 3/1986 | Kreamer | 606/200 |
| 4,710,192 | 12/1987 | Liotta et al. | 623/11 |
| 4,793,348 | 12/1988 | Palmaz | 606/1 |
| 5,053,046 | 10/1991 | Janese | 606/213 |
| 5,061,274 | 10/1991 | Kensey | 606/215 |
| 5,116,357 | 5/1992 | Eberbach | 606/213 |

FOREIGN PATENT DOCUMENTS

| | | | |
|---|---|---|---|
| 2822603 | 11/1979 | Germany | 606/213 |
| WO90/14796 | 12/1990 | WIPO | 606/213 |

OTHER PUBLICATIONS

Rashkind, Taussig Lecture.

*Primary Examiner*—Stephen C. Pellegrino
*Assistant Examiner*—Jeffrey A. Schmidt
*Attorney, Agent, or Firm*—Richard J. Godlewski

[57] ABSTRACT

In connection with herniotomia or laparoscopy a device (12) for supporting the abdominal wall may be passed into the abdominal cavity through a percutaneously arranged guard tube (23) that is preferably inserted in the abdominal cavity through the hernial canal. The supporting device (12) includes a barrier material (13) which may for instance be a synthetic net. The supporting device has a stiffener (14) allowing such a controlled deformation of the barrier material that the supporting device may pass through the guard tube (23), following which the stiffener is capable of unfolding the barrier material into a substantially plane condition. After insertion and unfolding the supporting device (12) may be tightened against the peritoneum (26) by means of a thread (19) that may be fastened on the surface of the patient's skin.

17 Claims, 4 Drawing Sheets

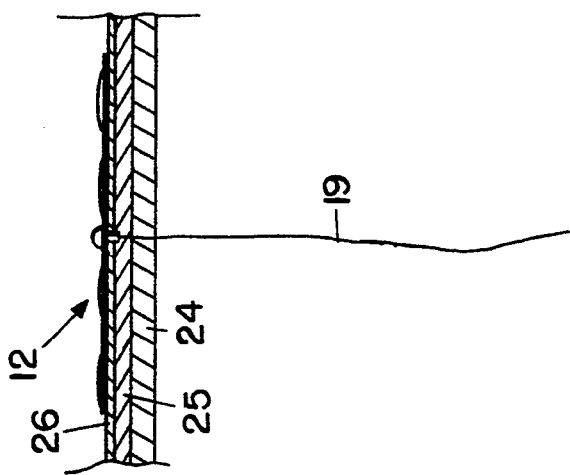
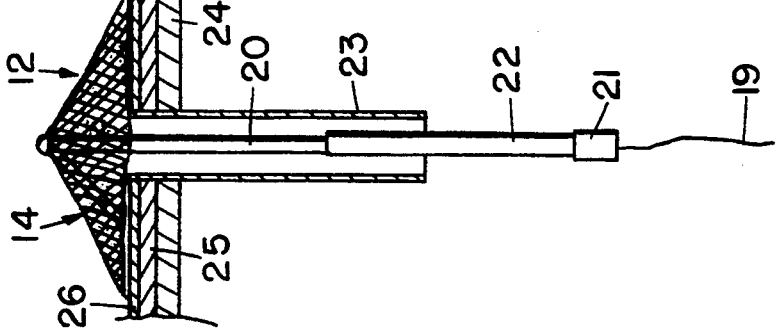
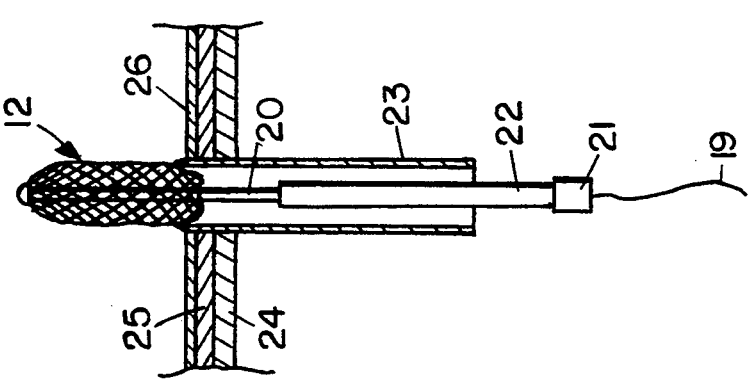
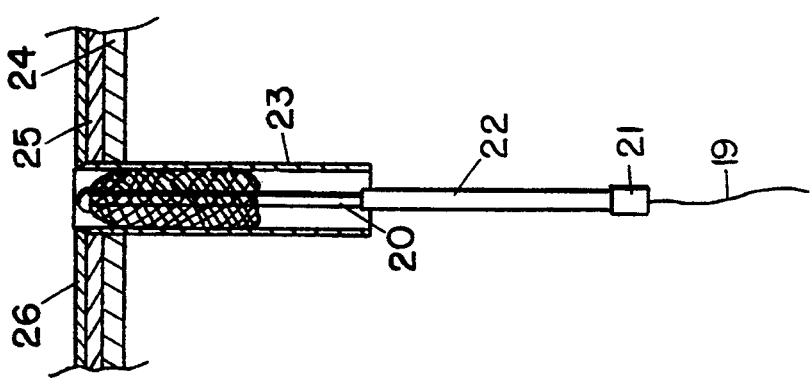

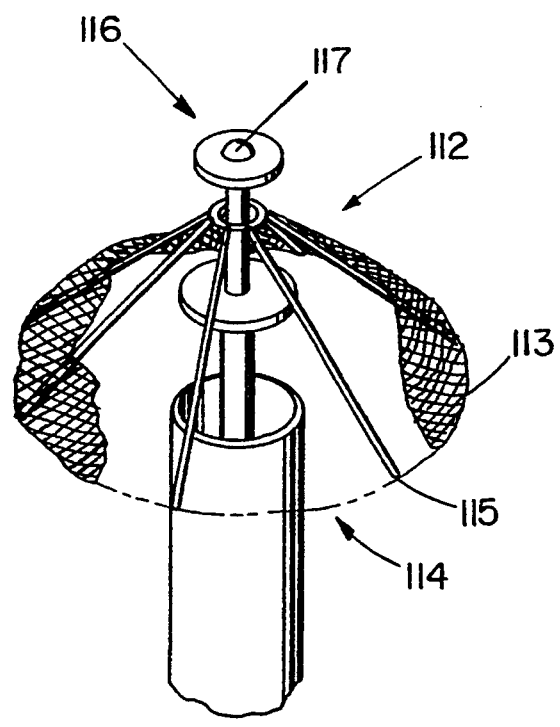
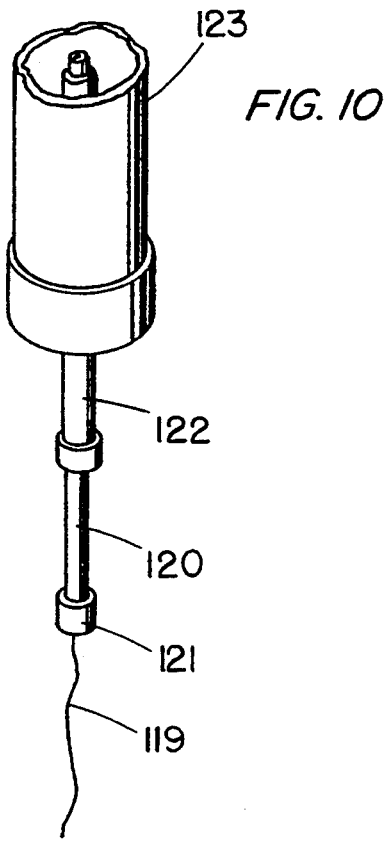
FIG. 10

SUPPORTING DEVICE AND APPARATUS FOR INSERTING THE DEVICE

RELATED APPLICATIONS

This application was originally filed in Denmark with Serial No. 1914/91 on Nov. 25, 1991 and is related to U.S. application Ser. No. 07/797,321 of Cesare Gianturco, filed concurrently on Nov. 25, 1991, both applications presently being assigned to a common assignee.

TECHNICAL FIELD

The invention relates to a supporting device for supporting a weak area of the abdominal wall in a patient, the device comprising a flexible barrier material to be positionally fixed at the weak area by means of a fixation means.

BACKGROUND OF THE INVENTION

A person may contract hernia if the abdominal wall has a weak area that is not capable of keeping the peritoneum in place when larger pressures occur in the abdominal cavity. When hernia occurs, a bulge on the peritoneum, the so-called hernial sac, has penetrated through an opening, called hernial ring, in the abdominal wall and into the hernial canal. In herniotomy (herniotomia) the hernial sac is passed out of the hernial canal and away from the hernial ring. In order to prevent recurrent hernia the abdominal wall may then be strengthened on a level with the hernial ring.

This strengthening has traditionally been effected by stitching a piece of tissue across the hernial ring. In recent surgery methods the herniotomy is effected percutaneously by means of an endoscope and one or more working channels, thereby avoiding proper cutting through the abdominal wall. It is a prerequisite of this technique that all of the objects necessary for the operation can be inserted in the abdominal cavity and manipulated intraperitoneally through comparatively thin tubes. The working channels may be established by cutting with a scalpel a small hole through the abdominal wall and inserting a tube in the hole. Alternatively a trocar may be used, in which case the working channel is delimited by a trocar sheath. For the sake of simplicity the working channel is hereinafter referred to as a trocar sheath.

From the article, "Improvement in Endoscopic Hernioplasty," from *Journal of Laparoendoscopic Surgery*, Volume 1, No. 2, 1991, it is known to make two incisions through the peritoneum on a level with the hernial ring and to pull a barrier material in the form of a synthetic patch through one incision and spread the patch over the hernial ring by means of gripper pincers, following which the two incisions in the abdominal wall are sutured.

From the conference, Advanced Laparoscopic Surgery: The International Experience, held in Indianapolis, U.S.A., in the period from 20 to 22 May 1991, a supporting device of the above mentioned type was referred to by Dr. John Corbitt in his Paper on "Repair Indirect Inguinal Hernia at Laparoscopy." After removal of the hernial sac John Corbitt fills up the hernial canal with a plug of rolled gauze, following which the hernial ring is closed by means of a net patch which by means of pincers are spread across the hernial ring and fixed to the abdominal wall by means of plastic or metal clips. Another lecturer at the conference, Dr. Maurice Arregui, practices a similar technique while positionally fixing the mesh patch at the hernial ring by suture.

It is a drawback of the above surgical methods that barrier material inserted through the trocar has to be spread manually across the hernial ring and fixed manually, as this manipulation is very time-consuming. When the net is positionally fixed by suture, the patient must still keep his bed after operation for 3 to 4 days in order to ensure healing.

When laparoscopy is used in the diagnostic or surgical treatment of a patient one or more trocar sheaths are inserted through the abdominal wall and the necessary equipments, such as a light source, a viewing telescope and surgical instruments, are passed into the abdominal cavity and manipulated through the trocar sheaths. However, the trocar sheaths may create weak areas in the abdominal wall due to their penetrating the wall and creating openings therein.

SUMMARY OF THE INVENTION

The object of the invention is to provide a supporting device which can be operated into a patient in a quick and simple manner and in an ambulant operation.

With this view the supporting device is characterized in that support sheet means such as barrier material includes spring resilient means such as a stiffener which, on one hand, in a substantially slightly loaded condition is capable of keeping the barrier material spread and, on the other hand, allows such a controlled deformation of the barrier material that the supporting device may be received within a comparatively thin tube.

In view of the fact that the stiffener allows the supporting device to be deformed in order to be received within a thin tube the device may be inserted interperitoneally through a trocar sheath inserted in the abdominal wall, and the barrier material may at the same time be positioned in a spread condition at the weak area. Due to the stiffener only a very small manipulation of the supporting device is required in order to arrange it in the desired position. Moreover, it is unnecessary to fix the edge of the barrier material to the abdominal wall by suture or similar fixing means because the stiffener prevents a postoperative crumpling of the barrier material.

In a particularly simple embodiment the stiffener includes at least two mutually angled, flexible wires which in a non-deformed condition keep the barrier material spread in a substantially plane position. In view of the fact that the wires are resilient the stiffener may be doubled up without any permanent deformation when the supporting device is inserted in the thin tube. When the supporting device has been inserted in the abdominal cavity the stiffener straightens out after release from the trocar sheath, thereby spreading the material without manual assistance.

The simple and quick handling of the supporting device may further be promoted in that centrally in the spread material there is embedded a fastening means from which the stiffener extends, and in that the fixation means is a thread fixed at the fastening means. In a herniotomy, this embodiment of the device may be used in the following manner. After insertion in the abdominal cavity the device with the fastening means is positioned opposite the hernial ring and the thread is passed through the hernial canal and out onto the surface of patient's skin, pulling there at the thread until the barrier material spread by the stiffener abuts on the peritoneum and bars the hernial ring, following which the thread is fastened on the surface of the skin. It is not necessary to provide any further fixation of the supporting device.

In case the device is to be used to cure the weakness of the abdominal wall produced by the trocar sheath, the device is simply inserted in the abdominal cavity through the sheath. The thread then runs from the device through the sheath and onwards outside the patient where a slight pull at the thread causes the device to abut on the peritoneum, following which the trocar sheath is pulled out and the thread is fastened on the skin surface. The spread barrier material supports the abdominal wall in the weak area.

If the supporting device in the herniotomy is inserted through a working channel extending through the abdominal wall at a distance from the hernial canal, the device must be intraperitoneally positioned opposite the hernial ring. In this case the fixation may advantageously be facilitated in that the thread at a distance from the fastening means is fixed to a needle which from the interior of the abdominal cavity may be passed through the hernial canal and in the desired point be pushed through all the tissue layers until it perforates the skin and may be pulled out onto the surface of the patient together with the thread that is being drawn tight while simultaneously positioning the supporting device across the hernial ring. Alternatively a thin needle may be introduced percutaneously from the outside through the hernial canal in order to catch the thread which is subsequently pulled out outside of the patient together with the needle.

In a preferred embodiment the stiffener is made from a material with superelastic properties, preferably the shape memory alloy nitinol. The shape memory material may at a comparatively high temperature be easily set in any desired shape, e.g. a loop shape or stelliform. In a lower temperature interval, the material shows superelastic properties allowing considerable deformation without imparting any permanent deformation to the material. When cooled below the lower limit of said temperature interval (below the transformation temperature of the material) the material temporarily loses its stiffness so that it may be freely formed. After reheating to the temperature interval the material remembers and regains its preset shape and its stiffness and superelastic properties. Nitinol further presents the advantage of being well suited for implantation in the human body. The stiffener material preferably has its transformation temperature selected well below the body temperature of the patient and the superelasticity ensures that the barrier material will be spread out immediately after the intraperitoneal insertion of the device. However, it is also possible to select the transformation temperature only slightly below the body temperature of the patient, e.g. at 32° to 34° C. In this case, when the device after the intraperitoneal insertion is heated to the body temperature of 37°, the stiffener will suitably slowly straighten out in its predetermined shape and regain its stiffness. This offers time to the surgeon to position the supporting device at the hernial ring before the barrier material has been fully spread. The slow unfolding may also diminish the risk of damaging the intestines and peritoneum.

The invention further relates to an apparatus for percutaneous insertion of the supporting device, characterized in that the device is releasably fastened to one end of a carrying tube, the other end of which has a radially protruding abutment for a shorter guide tube journalled longitudinally displaceably about the carrying tube. When the carrying tube with the attached supporting device is inserted in the abdominal cavity the guide tube may be displaced forward to push the device free of the carrying tube, following which both tubes may be withdrawn from the abdominal cavity. This apparatus makes it possible to operate the supporting device into the patient in a particularly simple manner after a trocar sheath has been inserted through the abdominal wall, e.g. through the hernial canal, following which the apparatus is simply inserted through the sheath and the device is released in the position that is by and large correct as to fixation. It is thus not necessary to turn or manipulate the supporting device within the abdominal cavity.

BRIEF DESCRIPTION OF THE DRAWINGS

An example of an embodiment of the invention will now be explained in detail with reference to the schematical drawings, in which FIGS. 6 to 9 illustrate how the supporting device may be inserted and positioned during the surgical operation, and FIG. 10 is a pictorial view of another aspect of the present invention.

DETAILED DESCRIPTION

Figure 1:
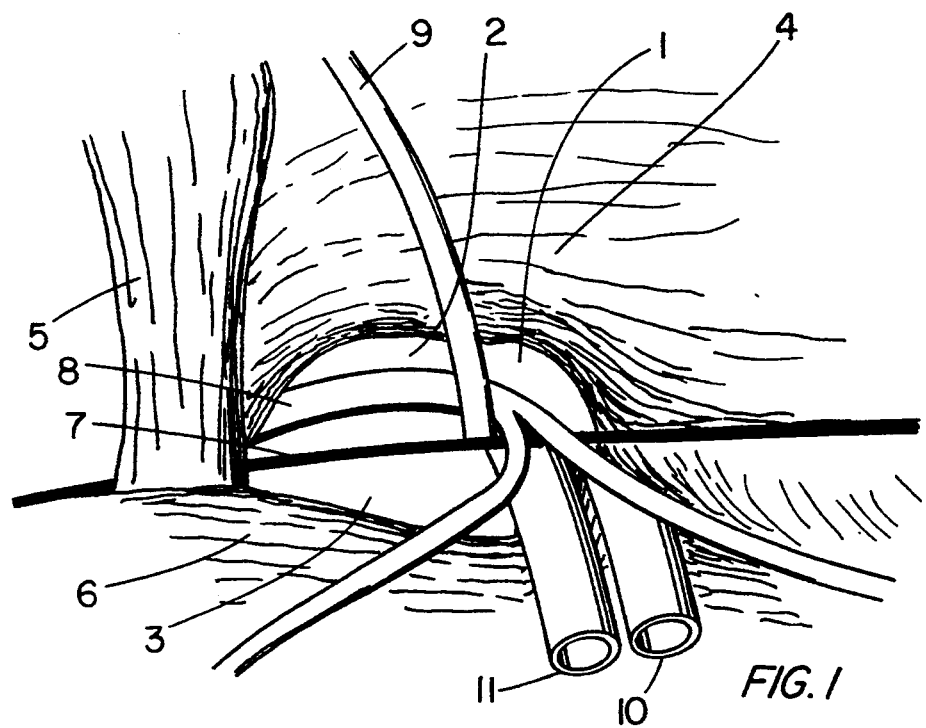
FIG. 1 shows the inguinal canal viewed from the inside of the abdominal cavity.

In the illustration shown in FIG. 1 of the inguinal canal in a male patient, the peritoneum and the transversal fascia have for the sake of clarity been cancelled. Three potential hernial rings are shown, viz. rings 1 and 2 for hernia inguinalis and the ring 3 for hernia femoralis. The circle 4 reflects the location of musculus obliquus internus and musculus transversalis, while the circle 5 reflects the location of musculus rectus. Hernial ring 3 is delimited by pubis and Cooper's ligament shown by 6 and by the inguinal ligament 7 which also delimits the two other hernial rings. The spermatic cord 8 extends upwards through the inguinal canal past the epigastric vessel 9 in Hesselbach's ligament and into the abdominal cavity. The femoral artery 10 and vein 11 are further shown.

Figure 2:
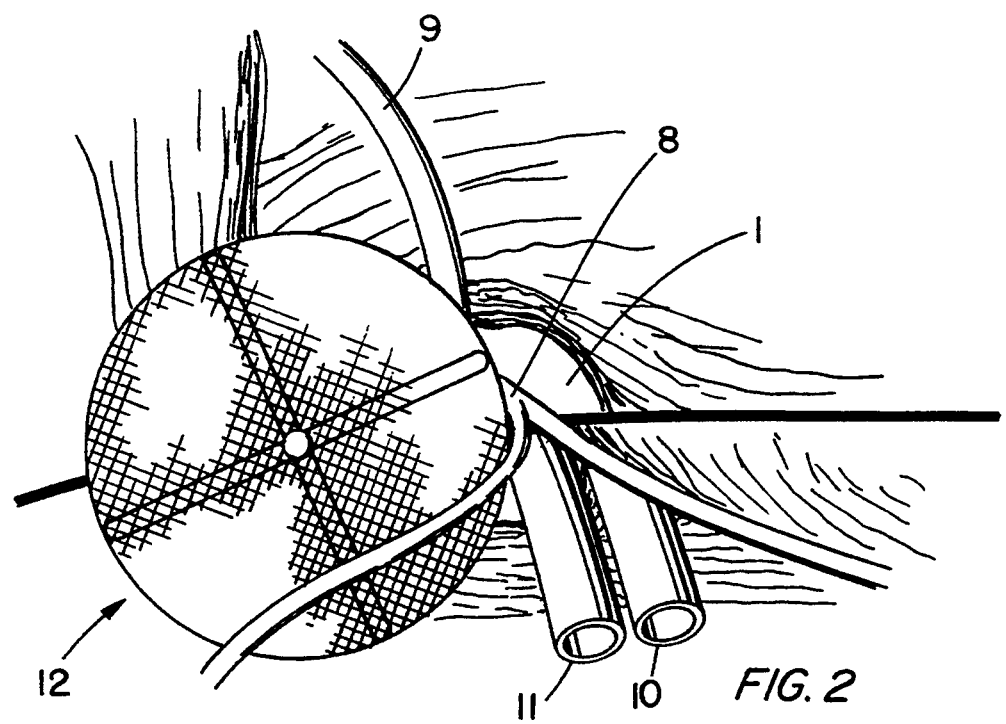
FIG. 2 is a corresponding illustration after the supporting device according to the invention has been fitted.
Figure 3:
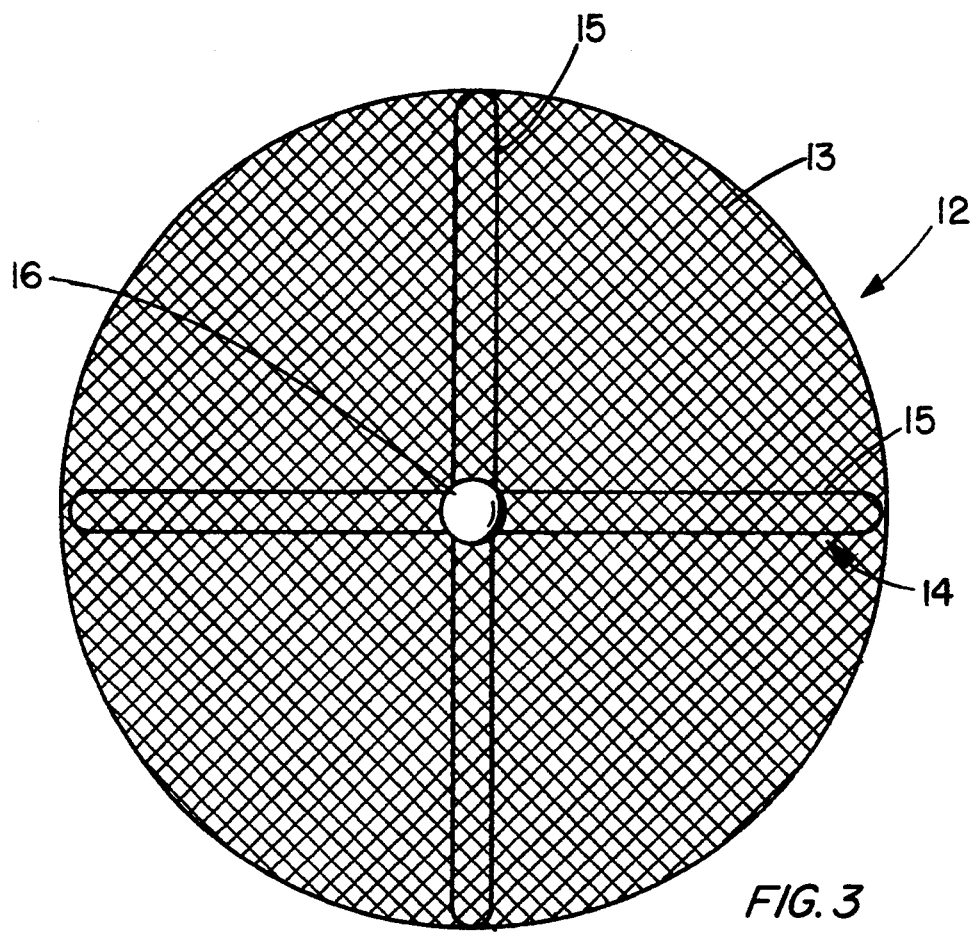
FIGS. 3 and 4 is a plane view and a side elevation, respectively, of the supporting device.
Figure 4:
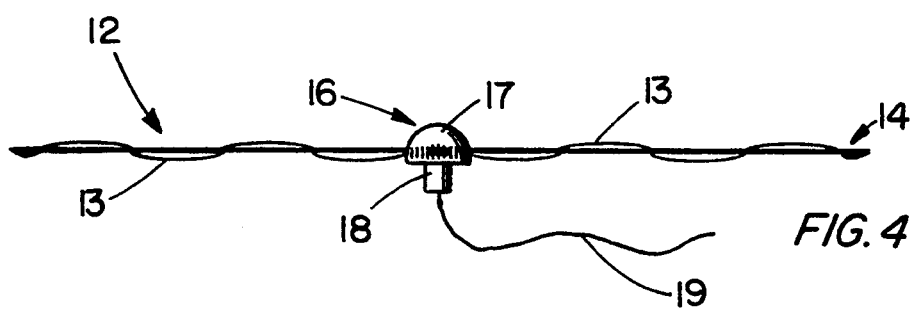

After a hernia the musculature around the inguinal canal is weakened, thereby increasing the risk of recurrent hernia. This may be eliminated by inserting, as shown in FIG. 2, tissue repair apparatus such as a supporting device generally designated 12 across the major part of the hernial ring, thereby preventing the peritoneum from penetrating through one of the hernial rings 1 to 3. The device 12 has such an appropriate size that it may abut on part of the musculature of the abdominal cavity and strengthen it, and that the spermatic cord 8, the femoral artery 10 and vein 11 together with the epigastric vessel 9 may concurrently pass freely by the device.

The barrier material of the device may be a guard of flexible synthetic material, in the illustrated design a support sheet or net 13 of polypropylene, mersutures or a biodegradable material such as a resorbable polyester, e.g. vicryl or resomer. The barrier material may alternatively be a thin, preferably circular piece of PTFE, e.g. gore-tex (soft tissue patch). Net 13 may be kept spread, mainly in a plane shape by spring resilient means such as a stiffener 14 consisting of a comparatively thin wire of the alloy nitinol that is a shape memory alloy which at an increased temperature, e g. at 500° C. may be set in a predetermined shape. By an appropriate composition of the alloy the transformation temperature may be selected to be, e.g. 10° C., so that the wire retains its superelasticity and stiffness during the manipulation and insertion into the abdominal cavity.

Stiffener 14 is advantageously composed of two wires either of which, as the predetermined shape, is formed as an elongate flattened loop 15. Due to this round shape the stiffener has no sharp edges or ends that may grasp and damage the tissue in the abdominal cavity. The net 13 is fixed to stiffener 14 in that the meshes are stuck in over the wire in loop 15 at uniform interspaces, and the two loops 15 extend transversely to each other in order to impart to the support sheet net the greatest possible stiffness.

In the middle of the net 13, a fastening means 16 is cast around loops 15 and the net proper. The means 16 may be made from silicone or a biodegradable polymer, such as synthetic or natural polymers (obtainable from e.g. Boehringer Ingelheim), or a resorbable polyester, e.g. vicryl or Resomer. The means 16 is on one side of the barrier material provided with a soft curvature 17 that cannot cause damage to the intestines in the abdominal cavity, and on the other side of the net means 16 has a pin 18 from whose end face a thread 19 extends which may for instance be made from vicryl.

The stiffener of the device may of course be designed in another way, e.g. as six radially extending arms 115 of device 112 disposed in a plane and uniformly distributed about fastening means 116 as depicted in FIG. 10. The designations 112–117 and 119–123 in FIG. 10 correspond to designations 12–17 and 19–23 in FIGS. 1–9. Alternatively, the stiffener can be a loop extending along the periphery of the net, which loop may be connected with the fastening means 16 through a number of spokelike arms. The stiffener may be made from stainless steel wire as well, or from a resilient plastic material.

Figure 5:
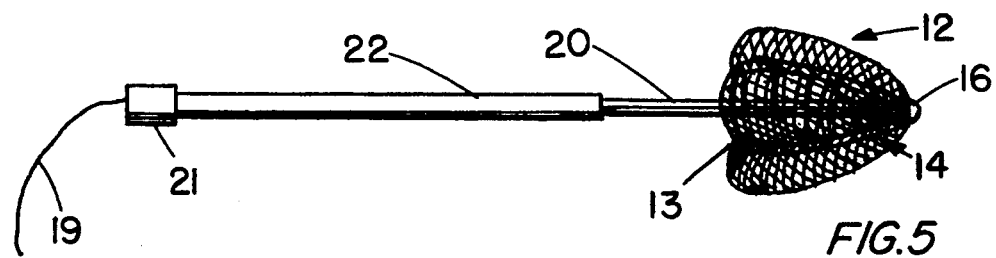
FIG. 5 is a side elevation of an apparatus according to the invention with a supporting device mounted thereon.

FIG. 5 shows introducing means such as an apparatus for the insertion of the supporting devices 12 and which is composed of an internal carrying tube 20 extending longitudinally through an external guide tube 22 that is somewhat shorter than tube 20. Pin 18 on fastening means 16 and the inner diameter of carrying tube 20 conforms to each other so that the pin upon insertion at one end of the carrying tube will be fixed thereon. The other end of the carrying tube has a radially protruding abutment 21 to confine the displacement of guide tube 22. The thread 19 that is considerably longer than tube 20 is passed centrally therethrough.

With reference to the very simplified FIGS. 6 to 9 it will now be described how the device may be operated into the patient.

The abdominal cavity is inflated with gas through a trocar so that the intestines are not positioned in the vicinity of the hernial ring. Then a trocar sheath 23 is percutaneously passed through the abdominal wall that may be composed of musculus obliquus externus and internus 24, musculus transversalis 25 and peritoneum 26. The hernial sac is then reduced.

The supporting device mounted at the end of the carrying tube 20 is introduced into the trocar sheath 23 while simultaneously folding the supporting sheet net 13 and spring resilient stiffener 14 round carrying tube 20, thereby allowing the device to pass through the trocar sheath 23. This folding-up has been made possible by the flexibility of the stiffener or by the circumstance that the stiffener is made from a shape memory alloy having superelastic properties. The apparatus is now pushed through sheath 23 and into the abdominal cavity, as illustrated in FIG. 7. When the edge of support sheet net 13 is freed from the internal end of sheath 23, stiffener 14 straightens the net as illustrated in FIGS. 8 and 9 until the net is substantially plane. This spreading-out may be effected as a consequence of the resiliency or stiffness of the stiffener.

When the supporting device 12 has been introduced into the abdominal cavity the guide tube 22 is moved inwardly to abut on fastening means 16, following which an inwardly directed push on guide tube 22 releases the supporting device 12 from carrying tube 20. Then, tubes 20 and 22 are at first removed and subsequently the trocar sheath 23 so that the tissue and the skin, not shown, close about thread 19 that has been pulled outwardly so that the supporting device 12 abuts on peritoneum 26 and bars hernial rings 1, 2 and 3.

If it is desired that the tissue of the abdominal cavity should grow together with net 13 and stiffener 14, the side of the barrier material facing away from the abdominal cavity may be coated with fibrinogen.

As mentioned above, it is also possible to insert the supporting device 12 through a trocar sheath passed through the abdominal cavity at a distance from the hernial ring. Some manipulation is, however, necessary in this case in order to position the supporting device at the hernial ring.

When the supporting device is to be used to support the abdominal wall in the area where the wall has been weakened by the insertion of the trocar sheath proper, the device may have more diminutive dimensions than in hernia applications. It will normally be sufficient if the barrier material in the spread-out condition is a few times wider than the diameter of the trocar sheath. This smaller device may be inserted and positioned in the same manner as described above with reference to FIGS. 6 to 9.

Naturally, the barrier material does not need to have the circular shape shown on the drawings but may be given any appropriate shape, such as oval, crescentic or rectangular.

What is claimed is:

1. A supporting device (12) for supporting a weak area of the abdominal wall in a patient, the device comprising a flexible barrier material (13, 14) to be positionally fixed at the weak area, characterized in that the barrier material includes a stiffener (14) of a superelastic material which, on one hand, in a substantially slightly loaded condition is capable of keeping the barrier material (13, 14) spread and, on the other hand, allows such a controlled deformation of the barrier material (13, 14); that the supporting device includes a comparatively thin tube (23); that the barrier material with the stiffener of superelastic material is introduced into the comparatively thin tube before insertion into the patient; and that the device further includes fixation means (19) centrally attached to at least one of the barrier material and the stiffener for affixing the device at the weak area.

2. A device as claimed in claim 1, characterized in that the stiffener (14) includes at least two mutually angled, flexible wires which in a non-deformed condition keep the barrier material spread in a planar position.

3. A device as claimed in claim 1, characterized in that centrally in the spread barrier material (13, 14) there is embedded a fastening means (16) from which the stiffener (14) extends, and in that the fixation means is a thread (19) fixed at the fastening means.

4. A device as claimed in claim 3, characterized in that the fastening means (16) is softly rounded off at a side of the barrier material that faces the intestines of the patient whereas an opposite side of the barrier material has a pin (18) extending perpendicularly from the barrier material when in a planar position and from which the thread (19) extends.

5. A device as claimed in claim 1, characterized in that a side of the barrier material (13, 14) is coated with fibrinogen.

6. An apparatus for percutaneous insertion of a supporting device as claimed in claim 1, characterized in that the supporting device (12) is releasably fastened to one end of a carrying tube (20) the other end of which has a radially protruding abutment (21) for a shorter guide tube (22) journalled longitudinally displaceably about the carrying tube.

7. An apparatus as claimed in claim 6 for the insertion of the supporting device, characterized in that the fixation means comprises a thread (19) that is passed longitudinally through the carrying tube (20) and has a substantially longer length than the carrying tube.

8. An apparatus as claimed in claim 6, characterized in that the barrier material with the stiffener before or during insertion into the patient is folded about the carrying tube (20) and is introduced into a guard tube, preferably a trocar sheath (23).

9. Tissue repair apparatus for providing a support for a weakened area (1, 2 or 3) of an abdominal wall of a patient, said apparatus comprising support sheet means (13;113) which, when in an expanded condition, serves to cover and protect the weakened area, characterized in that the tissue repair apparatus includes spring resilient means (14;114) of a superelastic material fixed relative to the support sheet means and serving to maintain the support sheet means under tension in the expanded condition and fixation means centrally attached to at least one of the support sheet means and the spring resilient means for affixing the apparatus at the weakened area; in that means (20,21,22,23;120,121,122,123) are provided for introducing the support sheet means in a folded compressed condition and the spring resilient means of superelastic material into the patient to the weakened area; and in that the spring resilient means serves to expand the support sheet means to the expanded condition after the introduction to the weakened area.

10. Apparatus according to claim 9, characterized in that the resilient means includes a plurality of mutually angled flexible wires (15;115) extending centrally from a fastening means (16;116) on the support sheet.

11. Apparatus according to claim 10, characterized in that the fixation means comprises a thread (19;119) for fastening the support sheet in a desired position and extends from the fastening means.

12. Apparatus according to claim 10, characterized in that the spring resilient means is made from nitinol.

13. Tissue repair apparatus for supporting a weakened area of an abdominal wall of a patient, comprising:
support sheet means when in an expanded condition for at least partially covering the weakened area;
spring resilient means of a superelastic material for maintaining the support sheet means under tension when in the expanded condition;
fixation means centrally attached to at least one of the support sheet means and the spring resilient means for affixing the apparatus to the abdominal wall proximate the weakened area; and
introducer means for introducing the support sheet means in a compressed condition and the spring resilient means of superelastic material into the patient.

14. The apparatus of claim 13 wherein the fixation means comprises a thread affixed to at least one of the support sheet means and the spring resilient means.

15. The apparatus of claim 13 further comprising fastening means positioned centrally to the support sheet means for extending the spring resilient means therefrom.

16. A supporting device (12) for supporting a weak area of the abdominal wall in a patient, the device comprising a flexible barrier material (13, 14) to be positionally fixed at the weak area, characterized in that the barrier material includes a stiffener (14) which, on one hand, in a substantially slightly loaded condition is capable of keeping the barrier material (13, 14) spread and, on the other hand, allows such a controlled deformation of the barrier material (13, 14) that the supporting device may be received within a comparatively thin tube (23), in that centrally in the spread barrier material (13, 14) there is embedded a fastening means (16) from which the stiffener (14) extends, in that the fixation means is a thread (19) fixed at the fastening means; in that the device further includes fixation means (19) centrally attached to at least one of the barrier material and the stiffener for affixing the device at the weak area; and in that the fastening means (16) is softly rounded off at a side of the barrier material that faces the intestines of the patient whereas an opposite side of the barrier material has a pin (18) extending perpendicularly from the barrier material when in a planar position and from which the thread (19) extends.

17. Tissue repair apparatus for providing a support for a weakened area (1, 2 or 3) of an abdominal wall of a patient, said apparatus comprising support sheet means (13;113) which, when in an expanded condition, serves to cover and protect the weakened area, characterized by spring resilient means (14;114) fixed relative to the support sheet means and serving to maintain the support sheet means under tension in the expanded condition and by fixation means centrally attached to at least one of the support sheet means and the spring resilient means for affixing the apparatus at the weakened area; characterized in that means (20,21,22,23;120,121,122,123) are provided for introducing the support sheet means in a folded compressed condition and the resilient means into the patient to the weakened area, in that the resilient means serves to expand the support sheet means to the expanded condition after the introduction to the weakened area; in that the resilient means includes a plurality of mutually angled flexible wires of superelastic material (15;115) extending centrally from a fastening means (16;116) on the support sheet; and in that the fixation means comprises a thread (19;119) for fastening the support sheet in a desired position and extends from the fastening means.

* * * * *